United States Patent [19]

Patel et al.

[11] Patent Number: 4,587,216

[45] Date of Patent: May 6, 1986

[54] MICROBIOLOGICAL OXIDATION REACTIONS USING PURIFIED MONOOXYGENASE ENZYME COMPONENTS

[75] Inventors: Ramesh N. Patel, Edison; Leonard E. Mortenson, Lebanon, both of N.J.

[73] Assignee: Exxon Research and Engineering Co., Florham Park, N.J.

[21] Appl. No.: 528,108

[22] Filed: Aug. 31, 1983

[51] Int. Cl.⁴ .................. C12P 17/02; C12P 7/26; C12P 7/22; C12P 7/04; C12N 9/02
[52] U.S. Cl. .................. 435/123; 435/148; 435/156; 435/157; 435/822; 435/189
[58] Field of Search .............. 435/189, 123, 148, 156, 435/157

[56] References Cited

U.S. PATENT DOCUMENTS 4,269,940 5/1981 Patel et al. .................. 435/148

FOREIGN PATENT DOCUMENTS 1603864 12/1981 United Kingdom .

OTHER PUBLICATIONS

Dalton in Advances in Applied Microbiology, vol. 26, pp. 71–87 (1980).
Colby et al, in Biochemical Journal, vol. 171, pp. 461–468.
Stirling et al, Biochemical Journal, vol. 177, pp. 361–364.
O'Connor et al, in Journal of General Microbiology, vol. 101, pp. 327–339 (1977).

*Primary Examiner*—Lionel M. Shapiro
*Attorney, Agent, or Firm*—J. E. Hasak; Ronald D. Hantman

[57] ABSTRACT

A purified hydroxylase enzyme component A of the methane monooxygenase enzyme isolated from the soluble fraction of *Methylobacterium organophilum* (CRL.26) (NRRL B-11,222) is found to contain three subunits. Any component A derived from methylotrophs having the particular characteristics of this isolated component A may be employed in conjunction with the flavoprotein component C of the methane monooxygenase enzyme, preferably the flavoportein component derived from the same organism, to catalyze the oxidation of various oxidizable organic substrates to their respective oxidation products. Preferably, the substrate is propylene.

15 Claims, No Drawings

MICROBIOLOGICAL OXIDATION REACTIONS USING PURIFIED MONOOXYGENASE ENZYME COMPONENTS

CROSS-REFERENCE TO RELATED APPLICATIONS

This application is related to copending U.S. Ser. No. 465,823 filed Feb. 14, 1983, which is a continuation-in-part application of copending U.S. Ser. No. 355,322 filed Mar. 8, 1982, now abandoned. These related applications disclose isolation of the soluble fraction of the faculative methylotroph *Methylobacterium organophilum* (CRL.26) (NRRL B-11,222) and its use in the oxidation of various substrates.

BACKGROUND OF THE INVENTION

The present invention relates to purified hydroxylase and flavoprotein components of the enzyme which may be found, for example, in the soluble fraction of *Methylobacterium organophilum* (CRL.26) (NNRL B-11,222). This invention also relates to a process for oxidizing organic substrates using a mixture of these two components.

Methane is one of the most inexpensive carbon sources for microbial growth. It is known that there are many microorganisms capable of growing on a culture medium in the presence of methane as the principal carbon source. However, not all of these microorganisms share good growth characteristics. It is also known that methane-grown microorganisms can be used to convert methane to methanol under aerobic conditions.

These methane-utilizing microorganisms are generally known as "methylotrophs". The classification system for methylotrophs proposed by R. Whittenbury et al. (*J. Gen. Microbiology*, 61, 205–218 (1970)) is the most widely recognized. In their system, the morphological characteristics of methane-oxidizing bacteria are divided into five groups: Methylosinus, Methylocystis, Methylomonas, Methylobacter and Methylococcus.

Recently, Patt et al. (*International J. Systematic Bacteriology*, 26, 226–229 (1976) disclosed that methylotrophic bacteria are those bacteria that can grow non-autotrophically using carbon compounds containing one or more carbon atoms but containing no carbon-carbon bonds. Patt et al. have proposed that methylotrophs should be considered "obligate" if they are capable of utilizing only carbon compounds containing no carbon-carbon bonds (e.g., methane, methanol, dimethylether, methylamines, etc.) as the sole sources of carbon and energy, whereas "facultative" methylotrophs are those organisms that can use both compounds containing no carbon-carbon bonds as well as compounds having carbon-carbon bonds as the sources of carbon and energy. In their paper, Patt et al. disclosed a methane-oxidizing bacterium, which they identified as *Methylobacterium organophilum* sp nov. (ATCC 27,886). This bacterium presumably differs from all previously described genera and species of methane-oxidizing bacteria because of its ability to utilize a variety of organic substrates with carbon-carbon bonds as sources of carbon and energy.

On the basis of $^{18}O_2$ incorporation from $^{18}O_2$ into the cellular constituents of *Pseudomonas methanica*, Leadbetter et al. (*Nature*, 184, 1428–1429 (1959)) suggested that the initial oxidative attack on methane involves an oxygenase. Higgins et al. (*J. Biochem.*, 118, 201–208 (1970) isolated $CH_3^{18}OH$ as the product of methane oxidation when suspensions of *Pseudomonas methanica* or *Methanomonas methanooxidans* were allowed to oxidize methane in $^{18}O_2$-enriched atmospheres. The subsequent observation of methane-stimulated NADH oxidation catalyzed by extracts of *Methylococcus capsulatus* by Ribbons (*J. Bacteriol.*, 122, 1351–1363 (1975)) suggested that the enzyme responsible for this oxygenation is a monooxygenase. These workers relied on indirect enzyme assays, measuring methane-stimulated NADH disappearance spectrophotometrically or methane-stimulated $O_2$ disappearance polarographically. Recently, methane monooxygenase systems were partially purified from the particulate fraction of *Methylosinus trichosporium* OB3b by Tonge et al., (*J. Biochem.*, 161, 333–444 (1977) and *FEBS Lett.*, 58 293–299 (1975)). Tonge et al. identified three components required for enzyme activity.

Hutchinson et al. (*J. Theor. Biol.*, 58, 325–335 (1976)) and Colby et al. (*J. Biochem.*, 157, 495–497 (1976)) reported that ethylene is oxidized by the soluble methane monooxygenase from *Methylococcus capsulatus* Strain Bath. The latter investigators reported that the "particulate membrane preparations" of *Methylococcus capsulatus* Strain Bath did not have methaneoxygenase activity as determined by the bromomethane disappearance test.

Subsequently, Colby et al. (*J. Biochem.*, 165, 395–402 (1977)) disclosed that the soluble fraction of the obligate *Methylococcus capsulatus* Strain Bath is a very non-specific oxygenase in that it oxidizes alkanes to alcohols, alkenes to 1,2-epoxides, dimethylether to ethanol and ethanal, styrene to styrene epoxide, and pyridine to pyridine N-oxide.

Most recently, Stirling et al. (*J. Biochem.*, 96, 205 (1979) and *J. Gen. Microbiol.*, 116, 277 (1980)) reported that the obligate methane-utilizing methylotroph, *Methylosinus trichosporium* OB3b, contained a soluble methane monooxygenase activity similar to that of the soluble methane monooxygenase from the *Methylococcus capsulatus* Strain Bath. U.K. Pat. No. 1,603,864 discloses a process for oxidation of selected organic substrates employing *Methylococcus capsulatus* or *Methylosinus trichosporium* as soluble fractions.

The methane monooxygenase enzyme from the organism *Methylococcus capsulatus* (Bath Strain) has been resolved into three component by DEAE-cellulose chromatography by Colby et al. (*Biochem. J.*, 171, 461 (1978)), Dalton (*Advances in Applied Microbiology*, 26, 71 (1980)) and Dalton et al. (*Flavins and Flavoproteins*, Massey and Williams, eds., Chapter 128, p. 763.) In the latter article the authors indicate that all three components A (a hydroxylase), B (an enzyme of molecular weight of about 15,000) and C (a flavoprotein) are necessary to catalyze the reductive oxygenation of the hydrocarobn substrate. The component A derived from the Bath Strain contains two subunits and has a molecular weight of about 200,000.

SUMMARY OF THE INVENTION

It has now been discovered that the soluble fraction of *Methylobacterium organophilum* (CRL.26) (NRRL B-11,222) described in cross-referenced U.S. Ser. Nos. 355,322 and 465,823 may be resolved into three components A–C, but that unexpectedly only components A and C are necessary to oxidize organic substrates to their oxidized products. Furthermore, the component A of this invention contains three rather than two subunits.

More generally, the present invention relates to a novel purified hydroxylase enzyme component A, isolated from the particulate or soluble extract of methylotrophic strains, which is characterized by having an average molecular weight of about 230,000±10,000 using gel-filtration and sedimentation equilibrium analysis and by having three subunits with average molecular weights estimated by polyacrylamide gel-electrophoresis in the presence of sodium dodecyl sulfate of about 58,000±5,000; 40,000±3,000; and 18,000±2,000 and by containing about 2.8±0.3 mole of iron per mole of protein.

This invention also relates to a mixture comprising component A as described above and a purified flavoprotein enzyme component C wherein the mixture is free or devoid of component B (which has a molecular weight of about 15,000). Component C is characterized by having an average molecular weight of about 38,000±4,000 using gel-filtration and sedimentation equilibrium analysis and by having one subunit with an average molecular weight as estimated by polyacrylamide gel-electrophoresis in the presence of sodium dodecyl sulfate of 38,000±4,000 and by having an absorption peak at about 450–460 nm and 390–395 nm and containing 1 mole FAD per mole of protein and 2 moles each of iron and acid-labile sulfide per mole of protein. Component C may be derived from the extract of the same organism from which component A was isolated or may be derived from other sources, so long as it has the above characteristics.

Finally, this invention describes a process for increasing the oxidative state of an oxidizable organic compound excluding alcohols which comprises oxidizing the compound, under aerobic conditions, in the presence of this mixture of components A and C and a cofactor system comprising $NADH_2$ or $NADPH_2$, until at least a portion of the corresponding oxidized product is produced in isolable amounts.

Thus, the mixture of components A and C is found sufficient to oxidize substrates without the need for component B, the counterpart of which is required in the mixed component enzyme system of Dalton and Colby using the Bath strain.

DETAILED DESCRIPTION OF THE PREFERRED EMBODIMENTS

The term "soluble fraction" refers to the enzyme activity in the supernatant solution obtained on harvesting the organism after growth in a fermentor (subsequent to growth in the shake flask) under continuous gassing with a mixture of a $C_1$ compound and air, when the broken cells are centrifuged at no less than 10,000×g. for at least 15 minutes. The term "particulate fraction" refers to the enzyme activity in the particulate extract obtained by the same procedure as above.

The term "increasing the oxidative state of an oxidizable organic compound" means incorporating oxygen in an organic compound, such as epoxidizing olefins and converting alkanes to alcohols or ketones. The enzyme herein will not by itself oxidize alcohols. The mixture of components purified from methane-grown microbial cells is preferably used to oxidize alkenes to the corresponding epoxides and alcohols, alkanes to the corresponding alcohols, ethers to the corresponding alcohols and aldehydes, benzene to phenol, and carbon monoxide to carbon dioxide.

The expression "cofactor system comprising $NADH_2$ or $NADPH_2$" as used herein refers to a system comprised of $NADH_2$ or $NADPH_2$ or equivalents thereof, i.e., systems which will (re)generate $NADH_2$ or $NADPH_2$ in the oxidation process. Thus, the above expression includes a cofactor system comprising $NAD^+$, a substrate and a $NAD^+$-linked dehydrogenase for the substrate, which system will regenerate $NADH_2$ in situ.

The source of the isolated components herein described is the particulate or soluble fraction of a methylotrophic facultative or obligate organism strain. The particular strain employed will determine the charateristics of the components. Thus, for example, component A from the *Methylococcus capsulatus* Bath Strain of Colby et al. is not the same component A as herein described, but component C from Colby et al. does meet the characteristics of component C as described herein. Thus, the mixture herein may contain component A as described herein from one source and component C from the Colby et al. source (or from other sources from which only component C can be obtained or from which both components can be obtained). The enzyme may be obtained from the particulate or soluble extract from the strain depending mainly on the conditions under which the strain is grown.

A preferred methylotrophic facultative organism strain which may be used as a source for both of the enzyme components herein described has the following identifying characteristics:

| Methylotrophic Organism Strain Name | ER & E Designation | U.S.D.A. Agriculture Research Center Designation |
|---|---|---|
| Methylobacterium Organophilum | (CRL-26 R6) [hereinafter (CRL.26)] | NRRL B-11,222 |

An important characteristic of this strain is its capability to produce microbial cells (white colonies in this case) when cultured under aerobic conditions in a liquid growth medium comprising assimilable sources of nitrogen and essential mineral salts in the presence of methane gas or a methyl-radical donating carbon-containing compound such as methanol, methylamine, methyl formate, methyl carbonate, dimethyl ether, etc. as the major carbon and energy source.

The above strain has been deposited at the United States Department of Agriclture, Agriculture Research Service, Northern Regional Research Laboratory (NRRL), Peoria, Ill. 61604 and has received from NRRL the individual NRRL designation as indicated above pursuant to a contract between NRRL and the assignee of this patent application (Exxon Research and Engineering Company (ER&E)). The contract with NRRL provides for permanent availability of the progeny of this strain to the public upon the issuance of the U.S. patent or the publication of any patent application corresponding to the U.S. patent which first describes and claims this strain, and that progeny of this strain will be made available to one determined by the U.S. Commissioner of Patents and Trademarks to be entitled thereto according to 35 USC 122 and the Commissioner's rules pertaining thereto (including 35 CFR 1.14, with particular reference to 886 OG 638). The assignee of the present application has agreed that if this strain on deposit should die or is destroyed during the effective life of the patent, it will be replaced with a living strain of the same organism. It should be understood, however, that the availability of a deposit does not constitute a license to practice the subject invention in derogation of patent rights granted by governmental action. U.S. Pat. Nos. 4,266,034; 4,241,184; 4,269,940; 4,375,515 and 4,347,319 present claims relating to this new microorganism, and the organism has been available to the public since Dec. 23, 1980.

Examples of other methylotrophic strains which may be employed as sources for both components A and C herein are *Methylobacterium organophilum* XX (ATCC 27,886), *Methylosinus trichosporium* OB3b (NRRL B-11,196) Methylococcus sp. (CRL.25) (NRRL B-11,221) and Methylosinus sp. (CRL.16) (NRRL B-11,203).

While all of the sources which will produce component C as described herein will not necessarily produce component A (e.g., the Bath strain), the skilled practitioner can readily determine which organisms will produce these components by following the steps outlined below to obtain, purify and characterize the components of the methylotrophic organism tested.

The strains which may be employed herein preferably are obtained from soil samples which are screened for methylotrophic microorganisms by growth under oxygen and methane. The methylotroph is then isolated, purified into a soluble or particulate extract, and maintained, and the soluble or particulate fraction is then resolved into its three components by the procedure described below.

The maintenance of the cultures of the organisms for use in the present invention should be carefully controlled. The preferred means for maintaining the cultures is described below.

The organism is preferably subcultured every two weeks on mineral salts agar plates which contain a medium having the following composition:

| | | |
|---|---|---|
| $Na_2HPO_4$ | 0.21 | g |
| $NaH_2PO_4$ | 0.09 | g |
| $NaNO_3$ | 2.0 | g |
| $MgSO_4.7H_2O$ | 0.2 | g |
| KCl | 0.04 | g |
| $CaCl_2$ | 0.015 | g |
| $FeSO_4.7H_2O$ | 1 | mg |
| $CuSO_4.5H_2O$ | 0.01 | mg |
| $H_3BO_4$ | 0.02 | mg |
| $MnSO_4.5H_2O$ | 0.14 | mg |
| $ZnSO_4$ | 0.02 | mg |
| $MoO_3$ | 0.02 | mg |
| Agar | 15 | g |
| Water | 1 | liter |

These plates should be incubated in glass dessicators which have lids with an airtight seal and external sleeves with a tooled hose connnection. Dessicators are to be evacuated and filled with a gas mixture of a $C_1$ compound, preferably methane, and air (1:1 v/v). Incubation should be at 30° C. Cultures will survive in these dessicators for three months at 4° C. However, frequent transfer of cultures is preferred.

In commercial processes for the propagation of microorganisms, it is generally necessary to proceed by stages. These stages may be few or many, depending on the nature of the process. Ordinarily, propagation is started by inoculating cells from a slant of a culture into a pre-sterilized nutrient medium usually contained in a shake flask. In the flask, growth of the microorganisms is encouraged by various means, e.g., shaking for thorough aeration, and maintenance of suitable temperature. This step or stage is repeated one or more times in flasks or vessels containing the same or larger volumes of nutrient medium. These stages may be conveniently referred to as culture development stages. The microorganism, with or without accompanying culture medium from the last development stage, may be introduced or inoculated into a large-scale fermentor to produce commercial quantities of the microorganism or enzymes therefrom.

Reasons for growing the microorganism in stages are manyfold, but are primarily dependent upon the conditions necessary for the growth of the microorganism and/or the production of enzymes therefrom. These include stability of the microorganism, proper nutrients, pH, osmotic relationships, degree of aeration, temperature and the maintenance of pure culture conditions during fermentation. For instance, to obtain maximum yields of the microbial cells, the conditions of fermentation in the final stage may have to be changed somewhat from those practiced to obtain growth of the microorganisms in the culture development stages. Maintaining the purity of the medium, also, is an extremely important consideration, especially where the fermentation is performed under aerobic conditions as in the case of the methylotroph microorganisms. If the fermentation is initially started in a large fermentor, a relatively long period of time will be needed to achieve an appreciable yield of microorganisms and/or oxygenase enzymes therefrom. This, of course, enhances the possibility of contamination of the medium and mutation of the microorganism.

The culture media used for growing the methylotrophic microorganism and inducing the oxidative enzyme system will be comprised of inorganic salts of phosphate, sulfates and nitrates as well as oxygen and a source of $C_1$ compounds. The fermentation will generally be conducted at temperatures ranging from 5° to about 50° C., preferably at temperatures ranging from about 25° to about 45° C. The pH of the culture medium should be controlled at a pH ranging from about 4 to 9 and preferably from about 5.5 to 8.5 and more preferably from 6.0 to 7.5. The fermentation may be conducted at atmospheric pressures, although higher pressures up to about 5 atmospheres and higher may be employed.

Typically, to grow the methylotrophic microorganism and to induce the oxygenase enzymes, the microorganism is inoculated into the medium which is contacted with a gas mixture containing methane and oxygen. Methane may be supplied in the form of natural gas. For continuous flow culture the microorganisms may be grown in any suitably adapted fermentation vessel, for example, a stirred baffled fermentor or sparged tower fermentor, which is provided either with internal cooling or an external recycle cooling loop. Fresh medium may be continuously pumped into the culture at rates equivalent to 0.02 to 1 culture volume per hour and the culture may be removed at a rate such that the volume of culture remains constant. A gas mixture containing methane and oxygen and possibly carbon dioxide or other gases is contacted with the medium preferably by bubbling continuously through a sparger at the base of the vessel. The source of oxygen for the culture may be air, oxygen or oxygen-enriched air. Spent gas may be removed from the head of the vessel. The spent gas may be recycled either through an external loop or internally by means of a gas inducer impeller. The gas flows and recycle should be arranged to give maximum utilization of methane.

The soluble fraction of the organism having enzyme activity is obtained by further culturing the organism, after growth in a shake flask, in a fermentor under specified conditions before harvesting thereof. Thus, a sterile liquid culture medium as described above which is charged to a fermentor is inoculated with the bacteria grown in the shake flask. The inoculated mixture is stirred while a continuous constant stream of filtered air and a $C_1$ compound, and initially carbon dioxide, is allowed to flow through the fermentor. The $C_1$ compound may be methane or any methyl-radical donating carbon-containing compound such as, e.g., methanol, methylamine, methyl formate, methyl carbonate, dimethyl ether or the like, but is preferably methane. In general, the ratio of $C_1$ compound to air, by volume, in the gaseous mixture used for growing the cells is preferably no greater than about 1:2, and most preferably between 1:6 and 1:8, to avoid unnecessary excesses of methane. The pH of the growth medium in the fermentor is maintained in the range of 6 to 9, preferably 6 to 8, and most preferably 6 to 7, to obtain a satisfactory rate of cell growth. When these conditions are maintained, the soluble fraction rather than the particulate fraction will generally contain the enzyme activity. If the growth takes place only in the shake flask, the enzyme activity will generally be contained in the particulate fraction.

After sufficient growth of the cells by either method, the organism is harvested. In a typical procedure the contents of the fermentor are removed and centrifuged to remove the water therefrom. The residual cellular solid is suspended in a buffer solution (pH about 6 to 9), washed, centrifuged and resuspended in the buffer solution. The cell suspension thus obtained is then disintegrated so that the cells are broken down. This is ordinarily and preferably accomplished in a French pressure cell into which the cell suspension is injected. The pressure cell, which is a block of steel with a piston and a chamber for the suspension, exerts a high pressure (e.g., up to 60 mPa or greater) on the suspension, and when the cell is opened, the rapid release of pressure causes the cells to disintegrate.

The disintegrated cells are separated into a particulate fraction and a supernatant (soluble fraction) solution by centrifuging the cell suspension at a force of at least $10,000 \times g$. for at least 15 minutes. In a preferred embodiment, the separation step is carried out by at least two centrifugation operations wherein the supernatant solution or particulate fraction from the first operation is centrifuged at a greater centrifugation force than was used for the first centrifugation. Especially preferred is isolation of the soluble or particulate fraction by two or a series of successive centrifugation at successively greater centrifugation forces up to a maximum force repesenting the mechanical limitation of the machine.

The enzyme-active fraction, whether particulate or soluble, is then resolved into its three components by ion-exchange column chromatography. One preferred method of resolution is to load the fraction on a DEAE-cellulose column (5 cm × 50 cm) equilibrated with a potassium phosphate buffer of pH of about 7 containing 5 millimolar dithiothreitol and 10% glycerol. The material not adsorbed to the DEAE-cellulose column, designated as component A (a hydroxylase), is eluted with this buffer and fractions containing component A are pooled. The column is then eluted with successive batches of the above-identified buffer containing 0.2M NaCl and 0.4M NaCl. Fractions from the 0.2M NaCl elute designated as component B are pooled, and fractions from the 0.4M NaCl elute designated as component C (flavoprotein) are pooled. During all the column chromatography and subsequent steps the buffer employed is purged with nitrogen.

Component A thus obtained is concentrated by an Amicon XM-100 membrane and loaded on a QAE-sephadex column which is equilibrated with the above-identified buffer. The column is washed with this buffer and eluted with the buffer containing 0.1M NaCl. Tubes containing component A are pooled and concentrated by Amicon XM 100 membrane filter. The concentrated hydroxylase A is passed through a Biogel-Agarose A-1.5 column which is equilibrated with the buffer. The active fractions containing component A are pooled, concentrated and stored in liquid nitrogen.

Component C from the DEAE cellulose column is concentrated by an Amicon PM 30 membrane and loaded on a DEAE-sephacel column equilibrated with the same buffer. The column is washed with the buffer and eluted with the buffer containing a linear gradient running from 0 to 0.5M NaCl in a total volume of 1 liter. Tubes containing component C are pooled, concentrated and passed through an Affigel blue of column equilibrated with the buffer. The column is washed with the same buffer and eluted with the buffer containing 2 mM NaDH. The active fractions thus eluted are pooled, concentrated and passed through a Biogel-Agarose A-1.5 column equilibrated with the buffer. The active fractions obtained after Biogel-Agarose column chromatography are concentrated by a Amicon PM-30 membrane and stored in liquid nitrogen.

When components A and C are thus purified, they are found to have the following properties:

The purified component A is a hydroxylase yielding a homogeneous single precipitin band on a Ouchterlony double diffusion plate with antisera. By ultracentrifugal analysis the Schlieren profile of component A reveals a single symmetrical peak. The sedimentation constant of hydroxylase is calculated to be 9.8 S. The average molecular weight as determined by gel-filtration on a Biogel-Agarose A-1.5 column and by sedimentation equilibrium analysis is about $230,000 \pm 10,000$. The average molecular weight of the subunits of component A as estimated by polyacrylamide gel-electrophoresis in the presence of sodium dodecyl sulfate is determined to be about $58,000 \pm 5,000$; $40,000 \pm 3,000$; and $18,000 \pm 2,000$, respectively. Component A contains $2.8 \pm 0.2$ mole of iron per mole of protein. A gamma-globulin fraction of antisera prepared against the purified component cross-reacts and inhibits methane monooxygenase activity as measured by the epoxidation of propylene.

Component C as purified by the above procedure is found to be a flavoprotein NADH reductase. The component yields a homogeneous single precipitin band on an Ouchterlony double diffusion plate with antisera. By ultracentrifugal analysis the Schlieren profile of component C reveals a single symmetrical peak. The sedimentation constant of the component is calculated to be 2.1 S. The average molecular weight as determined by gel-filtration on a Biogel-Agarose A 1.5 column and by sedimentation equilibrium analysis is about $38,000 \pm 2,000$. The average molecular weight of the subunit of the component as estimated by polyacrylamide gel-electrophoresis in the presence of sodium dodecyl sulfate is about $38,000 \pm 2,000$. The purified component C also has a spectroscopic absorption peak at 450–460 nm and 390–395 nm in the visible region. Component C contains 1 mole FAD per mole of protein and 2 moles each of iron and acid-labile sulfide per mole of protein. The purified component is directly reduced by a cofactor (NADH) under anaerobic conditions. During anaerobic titration of flavoprotein with NADH, a new spectral species appears in the 570 nm region indicating the formation of the neutral flavin semiquinone of FAD. An immunological fraction of antisera prepared against the purified component cross-reacts and inhibits methane monooxygenase activity as measured by the epoxidation of propylene.

When components A and C are mixed together in any relative amounts, preferably from 1:99 to 99:1 A:C by weight, more preferably from 50:50 to 80:20, and most preferably from 70:30 to 80:20, the resulting mixture is found to have significant activity for oxidizing various organic substrates. There is an optimum range of these components, but it is preferred to have more of component A than component C in the mixture. When component B is added to this mixture the activity of the mixture is not improved. Thus, the mixture herein is characterized by the absence of component B.

Tonge et al., supra, first reported the purification of methane monooxygenase from the particulate fractions of *Methylosinus trichosporium* OB3b. The two purified components were a particle bound component solubilized by phospholiphase D treatment and resolved into two protein components by ultrafiltration and a soluble carbon monoxide binding cytochrome C component. A three-component system purified from the same organism which catalyzed hydroxylation of methane consisted of the cytochrome C, a copper-containing protein and a small protein.

Colby et al., supra, reported a soluble methane monooxygenase from *Methylococcus capsulatus* (Bath strain) which was resolved into three components by ion-exchange column chromatography, all three of which were found required for enzyme activity. Component A had a molecular weight of about 220,000 and a subunit size molecular weight of 68,000 and 47,000. It contained 2 g-atoms of iron and acid-labile sulfide per mole. Component B was a colorless protein of 15,000 molecular weight. Component C was an iron flavoprotein of 44,000 molecular weight which contained 1 mole of FAD, 2 g-atoms of non-heme iron and 2 moles of acid-labile sulfide per mole of protein, similar to that discovered in this invention. The difference lies in the need of the Colby et al. system for component B to obtain enzyme activity.

Recently, Stirling et al. (*Biochem. J.*, 177, 361–364 (1979) and *Eur. J. Biochem.*, 96, 205–212 (1979)) demonstrated that *M. trichosporium* OB3b contains soluble methane monooxygenase activity similar to the Bath strain. In addition, Stirling et al. observed cross-reactivity between components B and C from *M. capsulatus* and component A from *M. trichosporium* OB3b.

The mixture of components A and C as described hereinabove is useful as an oxidizing agent when contacted with the desired oxidizable organic substrate (excluding alcohols), for example, a $C_2$–$C_4$ alkene, e.g., ethylene, propylene, butene-1 or conjugated butadiene or mixtures thereof, a cyclic compound such as cyclohexane, or an alkane such as methane, ethane, propane or butane, etc., in the presence of oxygen and a buffer solution or nutrient medium (e.g., the same nutrient medium used to produce the microorganism may be used except that the oxidizable substrate material has replaced the methane). The mixture is incubated until the desired degree of conversion has been obtained. Thereafter, the oxidized product is recovered by conventional means, e.g., distillation, etc.

Component A of this invention may not only be used in conjunction with component C but also may be used as an oxidizing agent in conjunction with other components isolated from other microorganisms which in admixture cross-react so as to have the requisite enzyme activity. Thus, for example, component A might be used in conjunction with components B and C of the Colby et al. Bath strain or with components B and C of the Stirling et al. OB3b strain.

The mixture of components A and C may be used to catalyze the oxidation of several oxidizable organic compounds, including oxidation of alkenes to the corresponding epoxides, e.g., ethylene to ethylene oxide, propylene to propylene oxide, 1-butene to 1,2-epoxybutane, butadiene to 1,2-epoxybutene, isobutene to epoxyisobutane, cis-but-2-ene to cis-2,3-epoxybutane and cis-2-buten-1-ol, trans-but-2-ene to trans-2,3-epoxybutane, etc., preferably, linear, branched, substituted, terminal or internal olefins. The mixture may also be used to promote oxidation of linear and branched alkanes to the corresponding primary, secondary or tertiary alcohols, such as, e.g., methane to methanol, ethane to ethanol, propane to 1-propanol and 2-propanol, butane to 1-butanol and 2-butanol, pentane to 1-pentanol and 2-pentanol, hexane to 1-hexanol and 2-hexanol, heptane to 1-heptanol and 2-heptanol, octane to 1-octanol and 2-octanol, isobutane to isobutanol and tert-butanol, cyclohexane to cyclohexanol, toluene to benzyl alcohol and cresol, etc., preferably linear, branched, cyclic or aryl alkanes. Additional oxidation reactions include oxidation of ethers to the corresponding alcohols and aldehydes such as, e.g., dimethylether to methanol and formaldehyde; substituted alkanes to aldehydes such as, e.g., chloro-, bromo-, or fluoromethanes to formaldehyde, oxidized dihalomethanes, and oxidized trihalomethanes; esters to the corresponding aldehydes, such as, e.g., methylformate to formaldehyde; benzene to phenol; and carbon monoxide to carbon dioxide. Alcohols cannot be oxidized.

The oxidation reactions using the mixture of components A and C must take place under aerobic conditions in the presence of a cofactor system comprising nicotinamide adenine dinucleotide in the reduced form ($NADH_2$) or nicotinamide adenine dinucleotide phosphate in the reduced form ($NADPH_2$). The cofactor which is initially present in the cell fraction is ordinarily removed therefrom during the purification process and must be replenished to effect oxidation using the mixture of components. The pH of the oxidation reaction using the mixture may range from 6 to 9, preferably 6–8, most preferably 6–7, and the temperature may range from about 20°–80° C., preferably 30°–50° C.

The $NADH_2$ cofactor system herein may be prepared by adding $NADH_2$ exogenously to the oxidation reaction mixture containing the enzyme component mixture or it may be generated (and/or regenerated) in situ. In the latter case, an $NAD^+$-linked dehydrogenase enzyme and its substrate may be used in the presence of $NAD^+$ to produce $NADH_2$ as electron donor for the enzyme. Examples of preferred cofactor systems for (re)generation of $NADH_2$ include a system of formaldehyde, $NAD^+$ and formaldehyde dehydrogenase, or a system of a secondary alcohol, such as 2-butanol, NAD+, and an NAD+-linked secondary alcohol dehydrogenase.

To facilitate the necessary effective contact of oxygen and the enzyme, it is preferred, for best results, to introduce a strong, finely divided air stream into a vigorously stirred dispersion of substrate in the oxidation medium that generally contains water and a buffer in which the enzyme preparation or microorganism culture is suspended. The enzyme preparation may then be separated from the liquid medium, preferably by filtration or centrifugation. The resulting oxidized product may then generally be obtained.

The process of the invention may be carried out batchwise, semicontinuously, continuously, concurrently or countercurrently. Optionally, the suspension containing the enzyme component mixture and buffer solution is passed downwardly with vigorous stirring countercurrently to an air stream rising in a tube reactor. The top layer is removed from the downflowing suspension, while culture and remaining buffer solution constituents are recycled, at least partly, with more oxidative substrate and addition of fresh enzyme preparation as required.

The growth of the methylotrophic microorganism and the oxidation process may be conveniently coupled by conducting them simultaneously, but separately and using much higher aeration in the oxidation process (e.g., an air excess of at least twice that required for growth, preferably at least five times as much aeration). Both the growth process and the methane hydroxylation or oxidation processes may be conducted in the same reactor in sequential or simultaneous operations by alternate use of normal and strong aeration.

The oxidation reaction should not be carried out in the presence of a substrate competing for the same enzyme system, and thus, none of the oxidation reactions should be carried out in the presence of methane except, of course, when methane is the substrate being oxidized to methanol.

The invention is illustrated further by the following examples which, however, are not to be taken as limiting in any respect. All parts and percentages, unless expressly stated otherwise, are by weight.

EXAMPLE 1

Preparation and Resolution of Soluble Fraction of Methane Monooxygenase From Facultative *Methylobacterium Organophilum* (CRL.26)

The facultative methane-utilizing organism, *Methylobacterium organophilum* (CRL.26), was isolated from soil samples by enrichment culture using methane (methane and air, 50:50 parts by volume) as a carbon source, as described in Patel et. al., *J. Bacteriol.*, 136, 352 (1978). The organisms were maintained on mineral salts agar plates in a dessicator under an atmosphere of 1:1 by volume of methane:air at 30° C.

The organisms were grown on a small scale at 30° C. in 2.8 liter flasks containing 800 ml of mineral salts medium with methane (1:1 parts by volume methane:air) as the sole carbon and energy source. Cells were harvested after 24–28 hours by centrifugation at 10,000×g. for 15 min. Large scale cultures were grown on methane at 30° C. in bath culture on a mineral salt medium in a 30-liter explosion resistant fermentor. The fermentor was inoculated with 5 liters of a culture grown in flasks. A gas mixture of 10% methane, 15% carbon dioxide and 75% air was continuously sparged into the fermentor. The pH was maintained at about 7.0 and the dissolved oxygen, carbon dioxide and methane were analyzed in the offgas system with an infrared analyzer.

The cells were washed twice with 25 millimolar potassium phosphate buffer at pH 7.0 and suspended in 25 millimolar potassium phosphate buffer at pH 7.0 containing 5 millimolar $MgCl_2$, 5 millimolar dithiothreitol, 10% glycerol and deoxyribonuclease (0.05 mg/ml). Cell suspensions at 4° C. were disintegrated by a single passage through a French pressure cell (American Instruments Co., Silver Spring, Md) at 60 mPa. Disintegrated cell suspensions were centrifuged at 40,000×g. for 60 min., yielding a soluble S(40) fraction. The soluble fraction was subsequently centrifuged at 80,000×g. for 60 min., yielding particulate P(80) and soluble S(80) fractions. The soluble S(80) fraction contained monooxygenase enzyme activity.

The soluble S(80) fraction was loaded on a DEAE cellulose (5 cm×50 cm) column equilibrated with 25 mM potassium phosphate buffer pH 7.0 containing 5 mM dithiothreitol and 10% glycerol (buffer A). The material not adsorbed to the DEAE-cellulose column, designated as fraction A or hydroxylase, was eluted with buffer A. Fractions containing activity of hydroxylase were pooled. The column was then eluted with successive batches of buffer A containing 0.2M NaCl and 0.4M NaCl. Fractions from 0.2M NaCl elute, designated as fraction B, were pooled, and fractions from 0.4M NaCl elute, designated as fraction C or flavoprotein, with a yellow color were pooled. During DEAE-cellulose column chromatography and all subsequent steps buffer A was purge with nitrogen.

The fraction A from DEAE-celloluse column chromatography was concentrated by Amicon XM-100 membrane and loaded on a QAE-sephadex column that had been equilibrated with buffer A. The column was washed with buffer A and eluted with buffer A containing 0.1M NaCl. Tubes containing activity of hydroxylase or fraction A were pooled and concentrated by Amicon XM 100 membrane filter. The concentrated hydroxylase was passed through a Biogel-Agarose A-1.5 column that had been equilibrated with buffer A. The active fractions containing hydroxylase activity were pooled, concentrated, and stored in liquid nitrogen.

The fraction C from DEAE cellulose column chromatography was concentrated by Amicon PM 30 membrane and loaded on a DEAE-sephacel column that had been equilibrated with buffer A. The column was washed with buffer A and eluted with buffer A containing a linear gradient running from 0–0.5M NaCl in a total volume of 1 liter. Tubes containing active fraction C (flavoprotein) were pooled, concentrated, and passed through an Affigel blue column that had been equilibrated with buffer A. The column was washed with the same buffer and eluted with buffer A containing 2 mM NADH. The active yellow fractions eluted with buffer containing NADH were pooled, concentrated, and passed through a Biogel-Agarose A-1.5 column that had been equilibrated with buffer A. The active fractions obtained after Biogel Agarose column chromatography were concentrated by Amicon PM-30 membrane and stored in a liquid nitrogen atmosphere. The component C thus obtained was purified about 70 fold from the soluble S(80) fraction.

EXAMPLE 2

Characteristics of Component A from Soluble Fraction of Methane Monooxygenase From CRL.26

Metal Analysis

A sample of purified component A from Example 1 was washed thoroughly with double glass distilled water in an Amicon ultrafiltration unit using a PM-10 membrane and finally diluted in 7 ml of total volume. Metal analysis was conducted using inductive coupled plasma atomic emission spectroscopy. A control consisting of double glass distilled water treated in a similar manner was employed. By this method component A was found to contain about 2.5 moles of iron per mole of protein.

Iron analysis carried out calorimetrically as described by Brumby et al., *Methods Enzymology*, 10, 463–474 (1967) revealed 3 moles of iron per mole of protein.

Immunological Properties

A gamma globulin fraction of antisera against purified component A was prepared as described by Meagher et al., *Biochemistry*, 12, 3523–3530 (1973). This fraction serologically cross-reacted with component A giving a homogeneous single precipitin band on Ouchterlony double diffusion plates. The gamma globulin fraction also inhibited methane monooxygenase activity of component A.

Ultracentrifugation Analysis

The sedimentation velocity of a solution of 9 mg/ml of purified component A from Example 1 was measured in a Spinco Model E ultracentrifuge at 58,000 rpm in buffer A at 40° C. The Schlieren profile of component A revealed a single symmetrical peak. The sedimentation constant ($S_{20}W$) of component A was calculated to be 9.8 S.

Molecular Weight and Subunit Size

The molecular weight of component A as determined by gel filtration on a Bio-gel agarose A-1.5 column was 220,000. Using sedimentation equilibrium analysis according to the procedure of Yphantis, *Biochemistry*, 3, 297–317 (1964) where the protein concentrations were successively 3, 6 and 9 mg/ml in 50 mM phosphate buffer of pH 7.0 containing 5 mM dithiothreitol, the molecular weight of component A was found to be 225,000. Thus, the average molecular weight of component A was 222,500±10,000.

The subunit molecular weight of component A was estimated by using polyacrylamide gel electrophoresis in a 12% gel system in the presence of sodium dodecyl sulfate. The samples were prepared as described by Weber et al., *J. Biol. Chem.*, 244, 4406–4412 (1969) except that the proteins were equilibrated with 50 mM tris-glycine of pH 7.0 containing 0.2% sodium dodecyl sulfate. The running buffer was 50 mM tris-glycine of pH 9.0 containing 0.2% sodium dodecyl sulfate. A constant voltage of 300 volts was applied for three hours. The gel was stained with 0.1% Amido black in 7% acetic acid—30% methanol and destained with the same solvent. Using the above technique the average molecular weights of the subunits of component A were estimated to be 58,000±5,000; 38,000±3,000; and 18,000±2,000.

EXAMPLE 3

Characteristics of Component C from Soluble Fraction of Methane Monooxygenase From CRL.26

Metal Analysis

A sample of purified component C from Example 1 was tested by the methods described in Example 2 for iron content and found to contain 2 moles of iron per mole of protein as determined by both plasma atomic emission spectroscopy and colorimetric analysis. Component C also contained 2 moles of acid-labile sulfide per mole of protein as determined by the method described by Chen et al., *Anal. Biochem.*, 79, 157–165 (1977).

Immunological Properties

When tested as described in Example 2 for immunological properties component C was found to behave similarly to component A in that the gamma-globulin fraction of antisera prepared against the purified component C cross-reacted with component C giving a single precipitin band and inhibited monooxygenase activity.

Ultracentrifugation Analysis

The sedimentation velocity of a solution of 8 mg/ml of purified component C from Example 1 was measured in a Spinco Model E ultracentrifuge at 59,800 rpm in buffer A at 4° C. The Schlieren profile of component C revealed a single symmetrical peak. The sedimentation constant ($S_{20}W$) of component C was calculated to be 2.1 S.

Molecular Weight and Subunit Size

The purified component C gave a single band of protein on a vertical 7% polyacrylamide gel-electrophoresis as described by Raymond, *Clin. Chem.*, 8, 455–470 (1962). The gel buffer was 50 mM tris-glycine of pH 9.0. Samples containing 50 micrograms protein, 30% sucrose and 5 microliters of 0.05% bromophenol blue in a total volume of 50 microliter were applied to the slot. A constant voltage of 300 volts was applied for 2 hours. The gel was stained with 0.1% Amido black in 7% acetic acid—30% methanol and destained with the same solvent. The molecular weight of component C as determined by gel-filtration on a Bio-gel agarose A-1.5 column was 40,000. Using sedimentation equilibrium analysis according to the procedure of Yphantis, supra, where experiments were carried out at 7000 rpm at 4° C. and the protein concentrations were successively 3 and 6 mg/ml in 50 mM phosphate buffer of pH 7.0 containing 5 mM dithiothreitol, the molecular weight of component C was found to be 38,000. Thus, the average molecular weight of component C was 38,000±4,000.

The size of the subunit of component C, estimated using the polyacrylamide gel electrophoresis technique described in Example 2, was calculated to be 40,000. This indicates that the flavoprotein of component C contains a single polypeptide.

Spectral Properties

Purified component C from Example 1 had an absorption peak at 460 nm and a shoulder at 395 nm in the visible region. In preparing a prosthetic group for fluorescence spectral analysis, a solution of component C was then dialyzed for 8 hours against glass-distilled water and the protein therein was precipitated by adding trichloroacetic acid thereto or by boiling in a water bath and was removed by centrifugation at 10,000×g. for 10 min. The yellowish green fluorescent supernatant thus obtained was diluted to the appropriate degree in 25 mM phosphate buffer of pH 7.0 for spectrophotometric or spectrofluorimetric analysis. The fluorescence excitation and emission spectra of the fluorescence supernatant had excitation peaks at 450 and 370 nm and also a single emission peak at 530 nm identical with the peaks found in authentic FAD.

Further identification of the prosthetic group as an FAD was established by thin-layer chromatography. The fluorescence material was spotted on a glass plate precoated with a layer of silica gel and developed with either 5% (w/v) $Na_2HPO_4.12H_2O$ or a mixture of 40 ml of a saturated $(NH_4)_2 SO_4$ solution, 9 ml of an 8% (w/v) sodium acetate solution and 2 ml of propan-2-ol. The fluorescence spots were detected under an ultraviolet lamp at 366 nm. The $R_f$ values in both solvent systems were identical with that of authentic FAD. The purified flavoprotein contained 1 mole of FAD per mole of protein assuming a molecular weight of protein of 40,000.

Reduction of Flavoprotein

Treatment of component C with an increasing concentration of NADH under anaerobic conditions resulted in a decrease in absorbance at 460 nm until the complete reduced spectrum was observed. An absorption peak appeared at 570 nm during the anaerobic reduction of flavoprotein by NADH which may be due to the formation of a neutral flavin semiquinone.

EXAMPLE 4

Oxidation of Propylene Using Purified Components A and C

The immunoglobulin fraction was separated from immune and normal rabbit serum by successive sodium sulfate fractionation followed by DEAE-cellulose column chromatography. The purified immunoglobin fraction was used for studies on inhibition of hydroxylase (A) and flavoprotein (C) activity. Varying amounts of the immunoglobulin fraction prepared against the hydroxylase and the flavoprotein were incubated with constant amounts of hydroxylase or flavoprotein, respectively, for 15 min. The immunoglobulin-treated hydroxylase (A) was then supplied for measuring the methane monooxygenase activity in the presence of component C by estimating the production of propylene oxide by the oxidation of propylene. Similarly, the imminoglobulin-treated flavoprotein (C) was supplied for measuring the methane monooxygenase activity in the presence of component A by measuring the epoxidation of propylene to propylene oxide.

Both components A and C were found to be necessary to catalyze the epoxidation of propylene to propylene oxide. Addition of component B to the mixture did not increase its enzymatic activity. It was found that the methane monooxygenase activity was directly dependent upon components A and C supplied in the reaction mixture. These results were obtained by carrying out the following procedure:

Several 3.0 ml vials at 40° C. were filled with 0.5 ml of a reaction mixture consisting of 25 micromoles potassium phosphate buffer at pH 7.0, an appropriate amount of $NADH_2$ and the components purified as described in Example 1 and indicated in Table I.

The vials were incubated at 35° C. on a reciprocating water bath shaker at 50 oscillations per minute. The gaseous phase of the vials was evacuated by vacuum and replaced with a 1 to 1 by volume gaseous mixture of propylene to oxygen, at which point the reaction was initiated.

The rate of epoxidation of propylene was measured by injecting 1-2 microliter samples of the reaction mixture into a gas chromatograph immediately after addition of substrate (zero time) and after 5 and 10 min. of incubation. Specific activities were expressed as nmoles of product formed per min. per mg. of protein, with the higher number representing better conversion. With each substrate, control experiments were conducted in the absence of $NADH_2$, in the absence of oxygen, and using a boiled reaction mixture.

The propylene oxide product was identified and estimated by retention time comparisons and cochromatography with authentic standards using flame-ionization gas chromatography. The column temperature was maintained isothermally at 110° C. with helium carrier gas flow rates of 20–40 ml per min. The amount of product formed was estimated from peak areas using a standard graph constructed using authentic compounds.

Protein concentrations in various fractions were estimated with Folin Ciocalteu reagent as described by O. H. Lowry et al., *J. Biol. Chem.*, 193, 265 (1951), using bovine serum albumin as a standard.

The results are indicated in Table I below.

TABLE I

| Component | Specific Activity (nmoles/min./mg of protein) |
|---|---|
| A* | 0 |
| B* | 0 |
| C* | 0 |
| A:B (75:25 by wt.)* | 0 |
| B:C (75:25 by wt.)* | 0 |
| A:C (75:25 by wt.) | 6200 |
| A:C:B (50:25:25 by wt.)* | 6200 |

*Comparative examples.

EXAMPLE 5

Components From Various Strains

I. Preparation of Fractions

Methylobacterium sp. (CRL.26) (NRRL B-11,222), *Methylobacterium organophilum* XX (ATCC 27,886), *Methylosinus trichosporium* OB3b (NRRL B-11,196), Methylococcus sp. (CRL.25) (NRRL B-11,221), and Methylosinus sp. (CRL.16) (NRRL B-11,203) were grown on methane as described above. Soluble S(40) and particulate P(40) fractions from cell suspensions of these methane utilizing organisms were prepared as described for Methylobacterium sp. (CRL.26) (NRRL B-11,222).

II. SDS-polyacrylamide gel-electrophoresis and electro-immunoblotting of hydroxylase and flavoprotein components of methane monooxygenase The purified hydroxylase and flavoprotein components of methane monooxygenase from Methylobacterium sp. (CRL.26) (NRRL B-11,222) and the soluble S(40) and particulate P(40) fractions were subjected to SDS polyacrylamide gel-electrophoresis in a 12% gel system as described by Laemmli, *Nature*, 227, 680 (1970). Proteins from the polyacrylamide gel were electrophoretically transferred to a nitrocellulose filter paper, and subsequently the nitrocellulose filter was treated with the immunoglobulin fraction of antisera prepared against the purified hydroxylase or the purified flavoprotein from the CRL.26 strain described above. The radiolabelled subunit proteins of the hydroxylase or flavoprotein component of methane monooxygenase in the soluble and particulate fractions of the various organisms were detected by radioiodinated protein A as described by Burnett, *Anal. Biochem.*, 112, 195-203 (1981). Radiolabelled bands were detected at about 60,000, 40,000 and 20,000 molecular size in the purified hydroxylase as well as in the soluble and particulate fractions of the above described methane-utilizing bacteria, corresponding to the subunit size of purified hydroxylase from Methylobacterium sp. (CRL.26) (NRRL B-11,222), upon treatment of the nitrocellulose filter with the hydroxylase immunoglobulin. This indicates that the hydroxylase protein component A from Methylobacterium sp. (CRL.26) (NRRL B-11,222) and the hydroxylase protein component A from the other above-described methane-utilizing bacteria are similar in subunit size, molecular weight, and antigenic properties.

Similarly, a radiolabelled band was detected at about 40,000 molecular weight in the purified flavoprotein component C as well as in the soluble and particulate fractions of the above-described methane-utilizing bacteria, corresponding to the molecular size of purified flavoprotein component C from Methylobacterium sp. (CRL.26) (NRRL B-11,222), upon treatment of the nitrocellulose filter with flavoprotein immunoglobulin. This indicates that the flavoprotein component C from Methylobacterium sp. (CRL.26) (NRRL B-11,222) and the flavoprotein C from the other above-described methane-utilizing bacteria are similar in molecular weight and antigenic properties.

What is claimed is:

1. A purified hydroxylase component A of a methane monooxygenase enzyme characterized by having an average molecular weight of about 222,500±10,000 and by having three subunits with average molecular weights as estimated by polyacrylamide gel-electrophoresis in the presence of sodium dodecyl sulfate of about 58,000±5,000; 38,000±3,000; and 18,000±2,000 and by containing about 2.8±0.3 moles of iron per mole of protein wherein said component is isolated from a soluble extract of a methylotrophic strain selected from the group consisting of *Methylobacterium organophilum* XX (ATCC 27,886), *Methylosinus trichosporium* OB3b (NRRL B-11,196), Methylococcus sp. (CRL.25) (NRRL B-11,221), Methylosinus sp. (CRL.16) (NRRL B-11,203) and *Methylobacterium organophilum* (CRL.26) (NRRL B-11,222).

2. The component of claim 1 isolated from a soluble extract comprising *Methylobacterium organophilum* (CRL.26) (NRRL B-11,222).

3. A mixture comprising the hydroxylase enzyme component A of a claim 1 and a purified flavo-protein component C of methane monooxygenase enzyme, said mixture being devoid of purified component B (having a molecular weight of about 15,000) of a methane monooxygenase enzyme, said component C characterized by having an average molecular weight of 38,000±4,000 and by having one subunit with an average molecular weight as estimated by polyacrylamide gel-electrophoresis in the presence of sodium dodecyl sulfate of 38,000±4,000 and by having absorption peaks at about 450-460 nm and 390-395 nm and containing 1 mole FAD per mole of protein and 2 moles each of iron and acid-labile sulfide per mole of protein, wherein said component is isolated from a soluble extract of a methylotrophic strain selected from the group consisting of *Methylobacterium organophilum* XX (ATCC 27,886), *Methylosinus trichosporium* OB3b (NRRL B-11,196) Methylococcus sp. (CRL.25) (NRRL B-11,221), Methylosinus sp. (CRL.16) (NRRL B-11,203) and *Methylobacterium organophilum* (CRL.26) (NRRL B-11,222).

4. The mixture of claim 3 wherein component C is isolated from a soluble extract comprising *Methylobacterium organophilum* (CRL.26) (NRRL B-11,222).

5. The mixture of claim 4 wherein component A is isolated from a soluble extract comprising *Methylobacterium organophilum* (CRL.26) (NRRL B-11,222).

6. The mixture of claim 3 containing from 1:99 to 99:1 by weight of components A:C.

7. The mixture of claim 3 containing from 50:50 to 80:20 by weight of components A:C.

8. A process for increasing the oxidative state of an oxidizable organic compound excluding alcohols which comprises oxidizing said compound, under aerobic conditions, in the presence of the mixture of claim 3 and a cofactor system comprising $NADH_2$ or $NADPH_2$, until at least a portion of the corresponding oxidized product is produced in isolable amounts.

9. The process of claim 8 wherein the mixture contains from 50:50 to 80:20 by weight of components A:C.

10. The process of claim 8 wherein during oxidation the pH ranges from about 6 to 9 and the temperature ranges from about 20° to 80° C.

11. The process of claim 8 wherein the oxidizable organic compound is selected from the group consisting of alkenes, alkanes, ethers, benzene, toluene and carbon monoxide.

12. The process of claim 11 wherein the alkene is a linear or branched alkene and the alkane is a linear, branched, cyclic or aryl alkane.

13. The process of claim 11 wherein the alkene is propylene.

14. The process of claim 8 wherein the $NADH_2$ or $NADPH_2$ is added exogenously to the oxidation reaction mixture.

15. The process of claim 8 wherein the $NADH_2$ is generated or regenerated in situ.

* * * * *